United States Patent [19]

Kaniecki

[11] 4,019,513

[45] Apr. 26, 1977

[54] AUTOMATED APPARATUS FOR SHAPING THE BEAK OR BILL OF YOUNG FOWL

[75] Inventor: Janeck Kaniecki, Pacy-sur-Eure, France

[73] Assignee: Jean Lissot, Pacy-sur-Eure, France

[22] Filed: Aug. 4, 1975

[21] Appl. No.: 601,423

[30] Foreign Application Priority Data

Aug. 7, 1974 France .......................... 74.27481

[52] U.S. Cl. .............................. 128/223; 128/253

[51] Int. Cl.[2] .................... A61B 17/00; A61D 1/00

[58] Field of Search ....... 128/173 R, 173 H, 172 R, 128/173.3, 213 R, 214 R, 216 R, 222, 223, 253, 303.1, 303.13, 303.14, 218 A; 119/22

[56] References Cited

UNITED STATES PATENTS

| | | | |
|---|---|---|---|
| 2,742,904 | 4/1956 | Lyon | 128/253 X |
| 3,434,474 | 3/1969 | Reynolds | 128/253 |
| 3,502,079 | 3/1970 | Simmons et al. | 128/253 |
| 3,570,487 | 3/1971 | Reynolds | 128/223 |
| 3,859,996 | 1/1975 | Mizzy et al. | 128/173 H |

FOREIGN PATENTS OR APPLICATIONS

| | | |
|---|---|---|
| 2,182,386 | 11/1973 | France |

*Primary Examiner*—Robert W. Michell

*Assistant Examiner*—Henry J. Recla

*Attorney, Agent, or Firm*—Baldwin, Wight & Brown

[57] ABSTRACT

Automated apparatus for shaping the beaks of young fowl and simultaneously giving them an oral injection. A backing member is mounted for generally horizontal arcuate movement and a red-hot blade is mounted for generally vertical arcuate movement. The upper half of the fowl's beak is put on the top of the backing member which is urged forward by force exerted on the fowl's body. A pneumatic circuit is controlled by this forward movement and actuates a pneumatic jack which moves the blade downward clamping and cutting the fowl's beak at least partially. With the downward movement of the blade an injection gun may be triggered and compressed air injects a vaccine into the fowl's oral cavity through suitable apertures in the backing member. Compressed air is also carried through the backing member to blow away severed bits of beak. After a predetermined interval the pneumatic circuit returns the blade to its initial position. The apparatus may also be providing with hypodermic injection means operating in unison with the oral injection means and the beak-shaping means.

11 Claims, 3 Drawing Figures

AUTOMATED APPARATUS FOR SHAPING THE BEAK OR BILL OF YOUNG FOWL

The present invention is related to an automated apparatus for shaping the beak or bill of young fowl.

Amongst treatments that young fowl or poultry, particularly chicks, are made to undergo, frequently figures a treatment for modifying the shape of the beak to make it less pointed thereby preventing them from pecking at one another when they have grown adult which is the source of a considerable number of deaths and in any event is of such a nature as to damage the quality of the flesh when they are raised for consumption.

Known devices for modifying the shape of the beak of fowl comprise a red-hot, more or less cutting, blade; the beak or only the upper half thereof is clamped between the blade and a fixed or movable backing surface thereby at the same time cutting and burning at the desired location.

Such devices are not automated and do not provide the required production rates for industrial breading where a labor force which is small in number and sometimes unskilled must treat a large number of fowl in a short period of time. Moreover, since the choice of the precise location where the beak is to be severed has to be determined for each case, it is inevitable that the beak or some fowl is cut too short which increases the rate of mortality by their refusal to eat, or too long which is ineffective for attaining the desired result.

The apparatus according to the present invention produces accelerated production rates and more accurate work and reduces the fatigue for the labor force.

Further, the apparatus provides combined automation of two distinct operations, i.e., shaping the beak and oral injection, which reduces stress and lessens the mortality rate in fowl so treated.

Finally, the design of the apparatus permits easy association with another device adapted to make a hypodermic injection further reducing stress, such operations being performed within a very short time interval, and also enables an increase in productivity and reduction in fatigue in the labor force by a logical organization of the work station.

An aspect of the apparatus according to the invention is that the backing member is displaceable forwardly and substantially horizontally, for instance, when it is pushed by a fowl's body, and that this displacement controls the vertical displacement of the heated blade for coming into contact with and, after a predetermined period of time, moving away from the backing member.

Preferably, the apparatus is supplied with compressed air which is used for functioning a pneumatic jack or cylinder for displacing the blade to be heated and also is carried inside the backing member for cooling it and is exhausted forward of the shaping surface for blowing away severed bits of beak. If only the upper half of the beak is to be shaped, there is advantageously provided oral injection means for vaccination or other purposes comprising an injection gun operated by the pneumatic jack, tubes for carrying liquid to be injected being connected to the injection gun, injection nozzles being connected to said tubes and disposed under the backing member and oriented so as to aim the injection liquid into the oral cavity of the fowl, and means for controlling injection at the same time as the beak-shaping operation.

An embodiment of the apparatus according to the invention will not be described relying on the accompanying drawings in which:

FIG. 3 is a perspective view of the backing member or platen.

Figure 1:
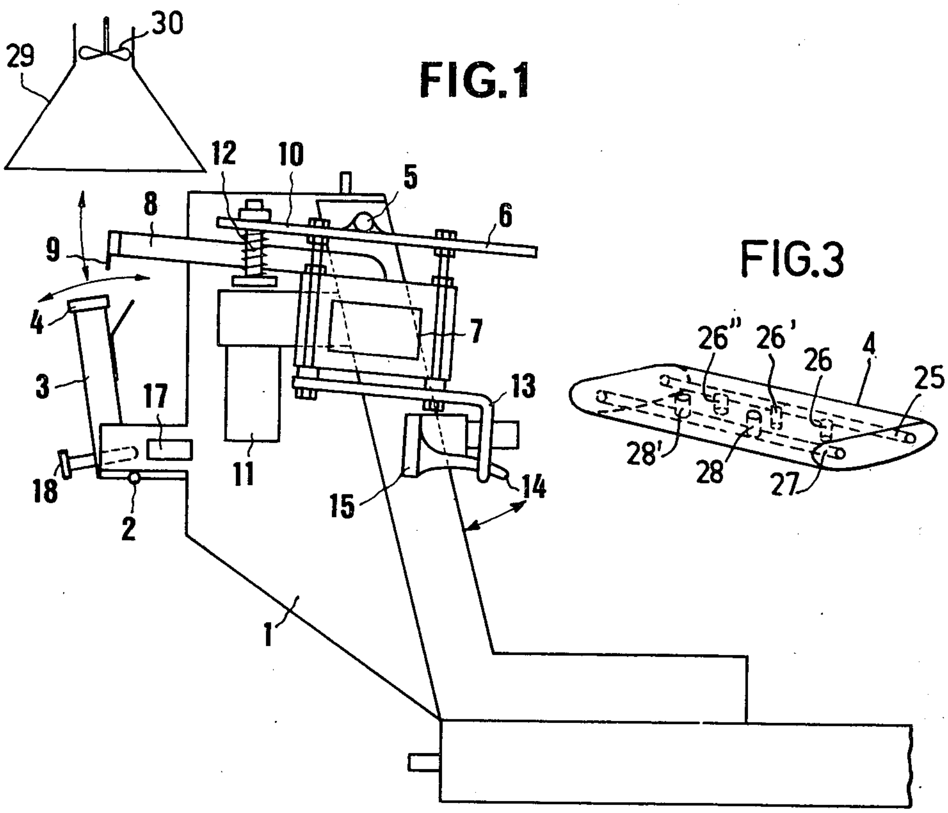
FIG. 1 is a schematic side view of the apparatus with the cover or enclosure removed.
Figure 2:
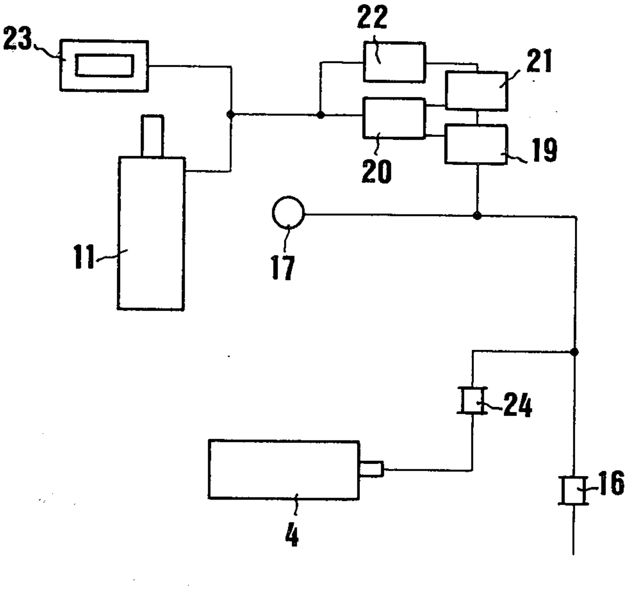
FIG. 2 is a block diagram illustrating the compressed air circuits.

The described apparatus, given by way of example, is adapted to shape the upper half of a chick's beak while simultaneously giving the chick an oral injection into its respiratory system.

The apparatus comprises a frame 1, a horizontal pivot member 2 for pivotally mounting a support 3 provided with a platen member 4 which constitutes the backing member. The platen member is replaceable so as to be adaptable to the morphology of different species and breeds. The platen member 4 is located nearly directly above the pivot member 2 and describes in movement thereabout a substantially horizontal circular arc.

Another movable assembly may pivot about another horizontal pivot 5, parallel to the pivot member 2. The assembly comprises a support member 6 pivotally mounted on the pivot 5 and supporting a low-voltage transformer 7, a blade support arm 8 carrying a heated blade 9 connected by insulated wires (not shown) to the secondary of the transformer 7. By pivoting about the pivot 5, the blade 9 describes a circular arc which is substantially vertical.

An extension 10 of the support member 6 is connected to a pull-type pneumatic jack 11 with a return spring 12.

Another extension 13 from the support member 6 functions to lift a trigger of the injection gun 15 when the jack 11 swings an whose assembly. The injection gun 15 is connected to a source of injection liquid and also, by a flexible tube (not illustrated), to the platen member 4.

The compressed air circuitry or unit of the apparatus comprises a pressure regulating valve 16 adapted to provide a constant pressure independent of the supply of compressed air, which pressure is adjustable as a function of the operative conditions, a drain or bleed detector 17 fixed to the frame 1 proximate to the support 3 being adapted to be closed off by the end of an adjustment screw 18 carried on the support 3. The function of the adjustment screw 18 is the precision adjustment of the point where the forward movement of the platen member 4 ends thereby fixing the length of the beak to be cut.

The bleed or drain detector 17 controls a YES cell 19 which in turn controls a compressed-air "generator" 20 which supplies compressed air to the pneumatic jack 11 and also a variable time delay element 21 which after a suitable time delay cuts off the flow of compressed air to the pneumatic jack 11 and actuates a bleed generator 22 which puts the circuit into communication with the ambient air for returning the system to the starting condition. A pulse counter 23 is mounted in parallel with the pneumatic jack 11. The component parts of the circuit are readily commercially available thereby appreciably reducing the production cost of the apparatus.

A branch circuit carries compressed air from the control valve 16 to the platen member 4 through a particular pressure regulator 24.

The platen member 4 is of elongate shape through which extend two parallel channels 25,27, the channel 25 communicating with the atmosphere through a series of downwardly inclined transverse apertures 26,26′,26″. The channel 25 is supplied with compressed air through the pressure regulator 24 which is exhausted through the transverse apertures 26,26′, 26″. The compressed air has a dual role: cooling the platen member, and blowing away through the transverse apertures the cut bits of beak to the ground. The other channel 27 in the platen member communicates with the ambient atmosphere through transverse apertures 28,28′ which are inclined upwardly. Liquid to be injected is fed through apertures 28,28′ and injected from the injection gun 15 into the oral cavity of the fowl being treated.

The operation of the apparatus is as follows:

The operator holding a fowl in each of his hands opens the beak of each fowl by reflex action resulting from exerting pressure on each of their necks. The birds are put into position with the upper half of their beaks on the platen member 4 and the lower part of the beaks under the same; at the same time the platen member 4 is pushed forward to pivot it about the pivot member 2. The adjustment screw 18 shuts off the bleed detector 17 which triggers the action of the pneumatic jack 11. The support member 6 swings about its pivot 5 and the blade 9 which is heated red-hot severs the beak at the desired location. At the same time the trigger 14 is pulled for injecting the liquid into the oral cavity of the birds. After a predetermined time the blade 9 moves back up and the birds are taken away; the platen member moves back to its initial position, and the cycle can start again.

The shape of the blade 9 and that of the platen member 4 must be adapted in each case for a particular bird; to avoid crushing the beak a guide member may be provided which may take the shape of a vertical plate pierced with holes of suitable configuration. Advantageously, there is provided a blade of rounded or chamfered shape so as to treat the most sensitive internal tissues of the beak. The blade 9 may be formed, for example, as a large diameter, round resistance wire.

The apparatus is advantageously provided with a hood 29 and a suction fan 30 in the vicinity of the blade 9 for exhausting fumes.

Finally, it is particularly advantageous to mount on such a "debeaking" apparatus another device for providing other injections. A compact unit is thereby constituted which permits intramuscular or hypodermic injections as well as the shaping of the beak and an oral injection within a short period of time without letting go of the fowl. This considerably diminishes adverse psychic effects due to repetitive painful treatments and known as stress whose nature is such as to increase the mortality rate.

The design of such apparatus, particularly since it can be connected to a single source of compressed air and since replacement parts are universal makes the combination especially advantageous.

What is claimed is:

1. An apparatus for shaping beaks of fowl, said apparatus comprising a blade, first support means mounting said blade for reciprocation along a path, a platen member for reception in the mouth of a fowl with the upper part of the beak of a fowl supported thereon, second support means mounting said platen member for movement between a retracted beak receiving position and a forward operative position aligned with the path of said blade means for varying the forward operative position of said platen member within the path of said blade to vary the length of a cut upper beak, drive means connected to said first support means for effecting reciprocation of said blade, and control means for said drive means, said control means including means responsive to movement of said second support means to said forward operative position whereby said blade reciprocates toward said platen member to trim an upper part of a beak to a predetermined length.

2. Apparatus according to claim 1, wherein said apparatus has means for treating two fowls at a time.

3. Apparatus according to claim 1, wherein said blade is of a configuration adapted for treating the internal tissues of the break.

4. Apparatus according to claim 3, wherein said blade is devoid of sharp corners.

5. Apparatus according to claim 1 wherein said control means includes a control element carried by said second support means for movement therewith for actuating said means responsive to movement, and said control element and said means responsive to movement include cooperable abutment surfaces for limiting said forward operative position of said platen member.

6. Apparatus according to claim 5 wherein said control element is adjustable to vary the forward operative position of said platen member.

7. Apparatus according to claim 1 wherein said drive means is in the form of a reciprocating drive motor.

8. Apparatus according to claim 1 wherein said control means includes timer means for actuating said drive means in a reverse direction after a predetermined time lapse.

9. Apparatus according to claim 1 wherein said platen member has orifice means for delivering a vaccine and like liquids into a fowl's oral cavity, injection means coupled to said orifice means, and injection control means for said injection means carried by said first support means for actuating said injection control means in response to movement of said first support means by said drive means.

10. Apparatus according to claim 1 wherein said drive means includes a spring return hydraulic jack, and said control means includes a source of pressurized fluid, means for allowing compressed fluid to be directed to said hydraulic jack, a control cell for controlling the actuation of said means for allowing compressed fluid to be directed to said hydraulic jack, bleed means for connecting said hydraulic jack to exhaust, a timer for actuating said bleed means, and said means responsive to movement of said second support means being a bleed device for controlling the actuation of said control cell and said timer.

* * * * *